United States Patent [19]

Cruz-Gómez et al.

[11] Patent Number: 5,948,934
[45] Date of Patent: Sep. 7, 1999

[54] PROCESS FOR RECYCLING POLYESTER OBTAINED FROM ORTO, META AND PARA BENCENDICARBOXILIC ACIDS

[75] Inventors: M.-Javier Cruz-Gómez, México, D.F.; Cecilia Rodriguez-Martinez, Tlalnepantla Edo. de México; Nicolás Ramirez-de-Arellano-Aburto, Naucalpan de Juárez Edo. de México, all of Mexico

[73] Assignee: Resinas y Materiales, Mexico

[21] Appl. No.: 09/002,405

[22] Filed: Jan. 2, 1998

Related U.S. Application Data

[63] Continuation of application No. 08/502,049, Jul. 14, 1995, abandoned.

[51] Int. Cl.$^6$ .................................................. C07C 67/02
[52] U.S. Cl. ............................................................. 560/78
[58] Field of Search ................................................ 560/78

[56] References Cited

U.S. PATENT DOCUMENTS 5,252,615 10/1993 Rao et al. .............................. 521/48.5

Primary Examiner—Samuel Barts
Attorney, Agent, or Firm—Locke Purnell Rain Harrell

[57] ABSTRACT

A process is disclosed for recycling of polyester used in the fabrication of molded plastic goods, such as films, carbonated beverage bottles and particularly waste poly(ethylene terephthalate) (PET) bottle grade, manufacturing residues and other manufactured articles. The process comprises the alcoholysis of washed or cleaned, crushed or grinded PET in one step of reaction, with alcohols containing from 1 to 4 carbon atoms in their molecule, in an autoclave reactor capable to support pressures of about 10 MPa (100 Kg/cm$^2$ gage) and operating temperatures in the range of 10 to 300° C.; followed by one or several steps of reaction product purification such as crystallization and/or centrifugation and/or distillation. The alcoholysis reaction product is a dialkyl aromatic ester (DAAE), which is recovered by filtration or centrifugation and depending on the alcohol used in the process the DAAE obtained are several industrial products such as dimethyl terephthalate, dibutyl terephthalate, etc. From the DAAE it is possible to obtain, through a transesterification reaction, plasticizers as dioctyl terephthalate and through a hydrolysis reaction, a pure terephthalic acid. From the process mother liquor it is possible to recover through distillation the pure process-alcohol and ethylene glycol and/or other different industrial glycols that were forming the PET molecules, and an industriallizable distillation residue.

11 Claims, 2 Drawing Sheets

5,948,934

PROCESS FOR RECYCLING POLYESTER OBTAINED FROM ORTO, META AND PARA BENCENDICARBOXILIC ACIDS

This is a continuation of application Ser. No. 08/502,049 filed Jul. 14, 1995 now abandoned.

TECHNICAL FIELD OF THE INVENTION

The present invention relates to a process for recycling molded plastic goods, as well as waste extrusion/inflated articles, particularly waste bottles made from poly(ethylene terephthalate), also known as bottle PET, and related copolymers.

BACKGROUND OF THE INVENTION

During the last 20 years, the carbonated beverage bottle industry has shown an increasing demand for the PET bottles, due to its lower weight and the fact the PET bottles show a higher rupture-resistance during the transportation, storage and handling of the carbonated beverages. The polymer known as bottle PET can be anyone of polyesters or copolyesters made with o-, m- or p-bencendicarboxilic acids. Those polymers are produced through the polycondensation reaction of those acids and/or its anhydride and/or its dimethyl esters with different glycols such as ethylene glycol and/or diethylene glycol and/or 1,4-bis(hydroximethyl)cyclohexene, also known as dimethanol-cyclohexane.

Carbonated beverage market distinguishes between two types of PET bottles: returnable and non-returnable bottles. After its use, empty non-returnable PET bottles are discarded to the garbage box, from where must be collected, sorted and cleaned for its recycling or otherwise land-fill disposed. On the other side, the U.S. Pat. No. 5,148,993 discloses that the returnable bottles are reused several times (3 to 5 for example) till the bottles separates them from service. The bottles are then crushed and/or grinded and then stored waiting for the polymeric material to be recycled. If the waste polymeric material is not recycled it is discarded as a non-biodegradable solid-waste to be accumulated in some place of the biosphere; otherwise they must be incinerated. Both, the accumulation and incineration are activities regarded as negative and noxious to the environment.

In some of the main industrial countries, with a relatively high rigid-polyurethane consumption, a process has been developed to transform the PET bottle polymer into a polyol of functionality equal to 2, which is useful in the production of polyurethane foams, by the depolymerization and transesterification of the polyester with diethyleneglycol, as disclosed in the U.S. Pat. No. 4,469,824. In the U.S. Pat. No. 5,095,145 terephthalic acid is produced, having developed a process for the production of terephthalic acid through hydrolysis of the bottle PET. In this process the steps of purification are delicate and complicate.

A theoretical solution exists for recycling clean waste product or intermediate wastes from the fiber grade polyester production process, through the depolymerization with low molecular weight alcohols, although those process were not economically feasible, since they implicated several steps of reaction and the stoichiometric raw materials yield was relatively low. For example, the U.S. Pat. Nos. 3,403,115 and 3,321,510 discloses process in this concern, but those innovations have not been exploited. Besides, those PET recycling innovations did not foresee any of the specific problems implied in the waste PET bottle recycling.

A need exists for a chemical process that treats molded plastic wastes, particularly of the polyesters made from the orto, meta and para-becendicarboxilic acids, known as bottle PET. This process should improve the yield of products from the raw materials and allows the recovery of high value chemicals, useful in ulterior manufacturing process. The process itself, as well as the waste material recycling purpose, should have acceptable ecological features.

SUMMARY OF THE INVENTION

A novel process is disclosed for the recycling of polymeric materials used in the fabrication of molded articles, particularly of polyester made from the ortho-, meta- and para-bencendicarboxilic acids. The process consists of: the chemical treating of washed, crushed or grinded PET in a reactor, with low molecular weight alcohols ($C_1$ to $C_4$); separation by filtration or centrifugation of the dialkyl aromatic ester (DAAE) as a main product, purification of the DAAE by crystallization in alcohol or distillation, fractional distillation and recovery of the resulting process mother liquor components such as the process alcohol, ethylene glycol and other glycols, that can be conveniently recovered for different applications.

Therefore, it is an object of the present invention to disclose a process for the recycling of polymeric wastes, particularly of polyester from the bencendicarboxilic acids, commonly called bottle PET.

Another object of the present invention is to disclose a process, that allows the high yield production of useful industrial products, from the recycling of waste articles made from poly(ethylene terephthalate), particularly bottle PET.

Other object of the present invention is to disclose a process for the industrial treatment of the waste PET bottles, allowing to solve a waste solids disposal problem.

A further object of the present invention is to disclose an economical process to avoid the environmental pollution caused by the waste plastic products.

These and other objects derived from the scope of the present invention will be better and in more detail understand with the following description.

BRIEF DESCRIPTION OF THE DRAWINGS

For a more complete understanding of the present invention, and for further details and advantages thereof, reference is now made to the following Detailed Description taken in conjunction with the accompanying drawings, in which.

DETAILED DESCRIPTION OF THE PREFERRED EMBODIMENTS

The present invention, as it has been mentioned, consist in a process for the recycling of carbonated beverages PET bottles, made from polyester from the o-, m-, and p-bencendicarboxilic acids and different glycols. Such a process comprises the steps of cleaning and grinding of the PET bottles. During the cleaning step the polyester is freed from level paper, metal caps, bottoms polyethylene, sand and any other foreign objects. The cleaning and/or mechanical separation of the components are of the public domain and made by hand, although they can be carried out by automated equipment, taking advantage of the ability of people versed in the art of treatment of refused plastics, for example as referred in the U.S. Pat. No. 5,148,993. The grinding step comprises the crushing and compacting of the clean PET bottles to convert them into polymer pieces with random dimensions. Any size of this polymer particles is good enough for the present process, although pieces with less than 10 cm (4 inches) side will be preferred.

Figure 1:
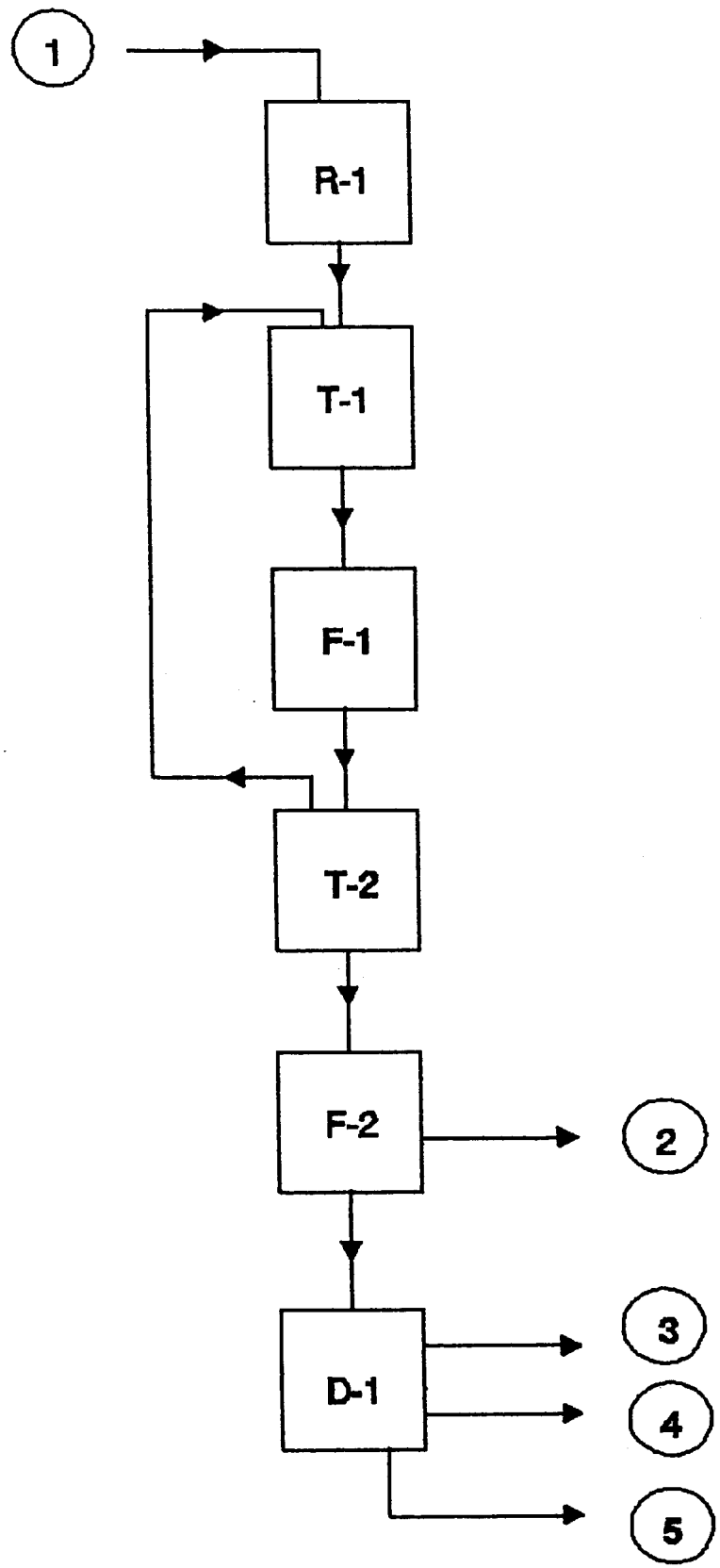
FIG. 1 represents a block diagram of a typical process, object of the present invention.

The recycling process of the bottle PET, which consist of polyester from the ortho and/or meta and/or para bencendicarboxilic acid and different glycols, consists of the steps, represented in the diagram from FIG. 1.

In a first step of the invention, after the above described mechanical preparation of the polymer load, the treatment is initiated by loading (1) the crushed PET, a low boiling point alcohol and a transesterification catalyst into the autoclave reactor (R-1). The alcohols useful for the present process are those with 1 to 4 carbons atoms, such as ethyl, methyl, n-butyl, iso- and n-propyl alcohols, among others. The transesterification catalysts are several organometalic compounds such as dibutyl tin oxide, cobalt, manganese and lithium acetate, the alkyl titanates such as tetrabutyl and tetrapropyl titanate. The reaction vessel is an autoclave (R-1). It is closed after loading. The reacting system is heated up to a preferred temperature between 200 to 300° C., till a homogeneous mixture is obtained and a fraction of the alcohol, loaded in excess, has been assimilated by the polyester. The time preferred for this reaction is from 10 to 100 minutes. During this time about 2 gram-mole of process alcohol are consumed for each 190 to 200 grams of loaded polyester. A preferred procedure is to load from 2 to 10 more parts of the chemically required alcohol. Once the reaction is finished the system is cooled down, and as consequence of this cooling the autoclave pressure goes down. The next steps consist in which a reaction product slurry is unloaded, which consists of solids suspended a mixture of process alcohol and glycols.

The slurry produced in the last step is received in a tank (T-1) with a heating jacket or coil, in which more process alcohol may be loaded, in order to dissolve all the dialkyl aromatic ester (DAAE) formed. The homogeneous solution formed has a DAAE content of about 1 to 35 weight percent and about 65 to 99 weight percent of alcohol plus glycols.

In the following step of the process and using the filtration system (F-1), the hot homogeneous solution produced in the last step is filtrated. Over the filtration system remain the mechanical impurities that could not be removed by the washing process previous to the alcoholysis which could came from the crushed bottle PET into the reactor, as well as any other solid present impurities up to this point of the process. Such impurities could be sand, catalyst salts, additives, pigments, among others. Trough the filter (F-1) runs a homogeneous solution having as a solvent the process alcohol and some glycol and as a solute the DAAE formed during the alcoholysis.

The following step consist in that, the filtrated solution are feeded to section (T-2) in which the excess alcohol is removed in order to form a high solids slurry. For this operation it can be used a commercial rotavapor or a distillation column. The alcohol is evaporated till only remains between 100 to 500 grams of alcohol per each 100 grams of reaction produced DAAE. The so produced slurry is cooled down to a temperature between 0 to 40° C. The recovered alcohol in (T-2) can be reused in (T-1) of the next batch processed.

In section (F-2) are separated through filtration or centrifugation both components of the previously formed slurry: DAAE solids and a mother liquor. The DAAE is the main process product. The mother liquor is a mixture of process alcohol, glycols, some dissolved DAAE and several other compound. The DAAE so produced can be used in several industrial process, such as: a). The production of the plasticizer dioctyl terephthalate, also known as DOTP, b). The pre-polymer or intermediate compound known as bis-(hydroxyethyl)terephthalate or BHET, used or needed by all the polycondensation process to make the same bottle PET polyester, chips of fiber-grade polyester and polyester fiber and c). The production of the organic acid from the DAAE known as terephthalic acid, by hydrolysis of the DAAE. In the process options a) and b), carried-out by transesterification of the DAAE with an alcohol or glycol, as well as in the process of c) carried-out by hydrolysis of the DAAE, in all of these processes it is regenerated the process consumed alcohol of step (R-1) of this invention. If a high purity is needed for the DAAE it is possible to repeat once again the purification steps that followed the reaction step, or to apply a DAAE distillation purification step to the alcoholysis reaction product, as it is described later below.

In the last section of the process(D-1), it is carried-out the separation and purification of the components from the process mother liquor by redistillation of the distillation cuts; among them: a light cut (3) where it is mainly found the process alcohol; an stream (4) generated in reactor (R-1) with several glycols, as ethylene glycol, diethylene glycol, in some cases the 1,4-bis(hydroximethyl)cyclohexane, and some others; and a stream called residue (5) which consists of a mixture of DAAE with different organic and inorganic compounds. This residue can be reprocessed to extract more DAAE or it can been used as raw material for some other industrial processes.

Figure 2:
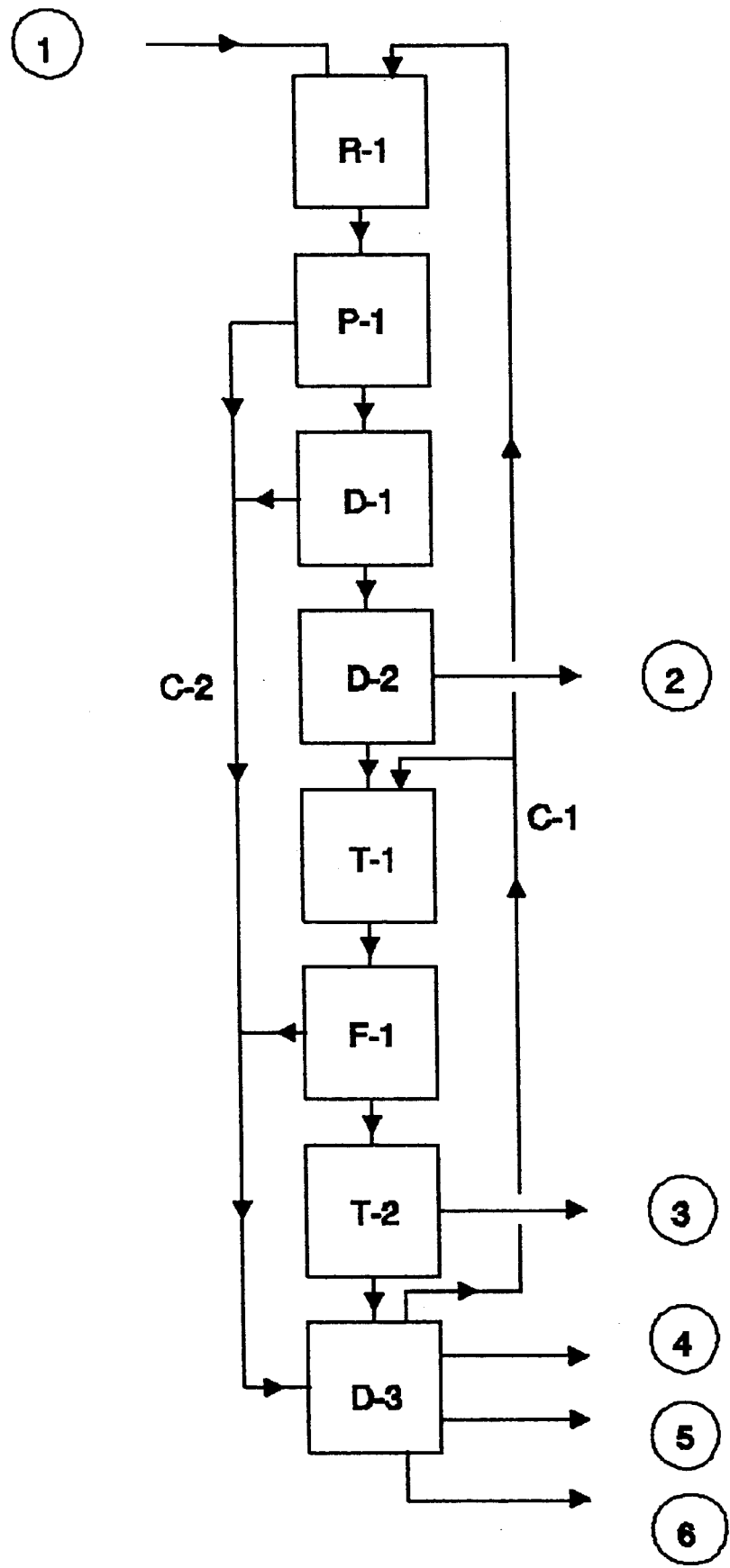
FIG. 2 shows one of the modalities of the present invention process.

In FIG. 2 it is shown a modality for the practical application of the present invention. This and other further modalities should be considered within the scope of the present invention, without any modification to the extend and spirit of the present invention.

In this way, the process described in the previous steps, can be performed from the practical point of view, in a continuous or semicontinuous industrial installation using not only the purification step through DAAE crystallization, but this step, followed or not by one or several steps of distillation, as it is shown in the process diagram of FIG. 2. Within this new modality the reactants are loaded into the autoclave (R-1) to carry-out the reaction in the same way as described for FIG. 1. The reaction product is separated in (P-1) into a crystallized solid and a liquid phase. In section (D-1) the wet DAAE are dried by evaporation of the remaining process alcohol. In the next section (D-2) the DAAE is distilled as an overhead product from a high boiling point residue as a bottoms stream (2). In accordance with the required purity for the DAAE there may or may not be used several steps of purification by crystallization in the process alcohol as follows for (T-1) and (F-1). In (T-1) the DAAE is dissolved with hot process alcohol, from where purer DAAE crystals are obtained by evaporation of some solvent and cooling down the system. The crystallization product is separated in (F-1) by filtration or centrifugation, into the solid DAAE and the mother liquor. The solid DAAE collected in (T-2) can be returned to (T-1) to receive a second purification process by dissolution, crystallization and filtration or centrifugation or it can be used in different industrial applications as: The production of BHET by reaction with ethylene glycol, the production of DOTP by reaction of the DAAE with 2-ethylhexilic alcohol or the production of terephthalic acid by reaction of the DAAE with water. For some specific applications of pure DAAE, this product can be melted in order to handle as a liquid with certain advantages. In section (D-3) are collected several streams (C-3) of process alcohol. The distilled process alcohol is recirculated to several steps of the process as (T-1) or (R-1). By the distillation of (D-3) are obtained several other cuts, like the streams of glycols (4) and (5) generated by reaction in (R-1) and a useful industrial residue.

The present invention is illustrated with more detail with the next process application examples, by using the figures attached to the document and a table for different operating conditions. It should be considered that the following examples are illustrations of some of the preferred modalities of the present invention.

EXAMPLE 1

In an autoclave with a volume of 650 ml, provided with a heating mantle, a thermowell with its thermomether, magnetic agitation and an internal cooling coil, there were loaded from 50 to 100 g of crushed bottle PET, 150 to 300 g of methanol and 0.010 to 0.100 g of zinc acetate, as it is recorded in the examples 1 and 2 of Table 1. During a period of time between 30 to 100 minutes, it was raised the temperature from 25 to 240° C. The system was kept at the last temperature for 90 minutes. Through the end of heating period it was registered a pressure of 6.5 MPa gage. As the reacting system was homogenized by agitation, the pressure system began to descend little by little fill it remained at 5.5 MPa gage. The heating mantle was shut-off to let the system to cool-down for about 40 minutes, till a temperature of 190° C. and a pressure of 1.5 MPa gage were reached. The cooling-down process was continued by a circulation of water through the cooling coil. Once the system reached a temperature of 60° C. and a pressure of 0 MPa gage the autoclave was opened to be unloaded.

EXAMPLE 2

In the example 2, as shown in the Table 1, it was followed the same procedure as in the example 1, except that the system was heated to 250° C. and kept then for only 30 minutes. With the reaction product of examples 1 and 2 there were obtained the same results in the process steps that follows.

The solids produced in the last step, along with excess methanol and glycols produced by reaction, were mixed with 1,200 g of methanol. By heating and stirring the last mixture it was obtained a homogeneous solution.

The homogeneous and hot solution obtained in the last step was filtrated. Over the filter were retained several solid, unsoluble impurities and below the filter was obtained a clear solution.

The clear solution was concentrated by recovering about 1,200 g of methanol. By cooling down the concentrated solution it was produced a suspended solid. For the three examples of Table 1 this solid was pure dimethyle terephthalate. The other components of the concentrated solution were methanol, water, monoethylene glycol and a small percentage of high molecular weight glycol.

In the next step of the process, it was separated by filtration the DAAE crystals obtained during the concentration and cooling-down of the filtrated solution. Per each weight unit of bottle PET loaded to the reactor there was obtained from 0.8 to 1.0 units of dimethyl terephthalate.

In the last step of the process, it was distilled the process mother liquor. Some extra methanol was obtained in this distillation. After, it was separated an intermediate cut with methanol, water and some glycol. Then, it was produced a monoethylene glycol cut. At the end of the distillation process and under an absolute pressure of less than 5 mm of Hg and a temperature greater than 240° C. it was obtained a few grams of high boiling glycol. Some residue was left in the bottoms of the distillation pot.

EXAMPLE 3

In the case of example 3, it was used a PARR™ autoclave with a volume of 2,000 ml, to which 200 g of crushed bottle PET were loaded. The operating procedure was the same that in the examples 1 and 2. The changes introduced because of the higher batch are enumerated in the Table 3 that follows. The catalyst used was 0.150 g of lithium acetate.

TABLE 1

OPERATING CONDITIONS FOR THE PROCESS REACTOR.

| No. | Concept | Example 1 | Example 2 | Example 3 |
|---|---|---|---|---|
| 1 | Crushed bottle PET loaded, g | 64.0 | 64.0 | 200.0 |
| 2 | Methanol loaded, g | 200.0 | 200.0 | 650.0 |
| 3 | Catalyst loaded, g | 0.064 | 0.064 | 0.150 |
| 4 | Volume of the reactor, ml | 650 | 650 | 2,000 |
| 5 | Reaction temperature, ° C. | 240 | 250 | 245 |
| 6 | Reaction time, minutes | 90 | 30 | 60 |
| 7 | Pressure during the reaction time, MPa gage | 60 ± 5 | 65 ± 5 | 58 ± 3 |

After several batches were collected of dimethyl terephthalate, produced in accordance with examples 1 to 3 of Table 1, it was dissolved in 2-ethylhexyl alcohol. The mixture was let to react at the proper temperature and pressure in order to produce a DOTP plasticizer under commercial specifications. In another experiment the DAAE produced by the process of this invention was let to react with pure water within an autoclave at a temperature of 250° C.; after separating by filtration a mixture of water and process alcohol, it was repeated the process of reacting the solids with more pure water, followed by filtration and drying of the retained solids; the solid produced in such a way was pure terephthalic acid. It is mentioned now, that the DOTP and the hydrolysis terephthalic acid are produced with dimethyl terephthalate; this is to corroborate that the DAAE produced by the process of the present invention are useful for the same type of applications that the DAAE actually found in the chemical industry market. With the process residue and diethylene glycol it is possible to make a viscous solution that under a temperature of about 200° C., reacts to produce a polyol useful in the manufacture of rigid polyurethane foams. Although preferred embodiments of the present invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the appended claims.

We claim:

1. A chemical process for treating polyesters of o-, m-, and p- bencendicarboxilic acids comprising:
   (a) mixing the polyesters and low boiling point alcohols;
   (b) alcoholysis of the polyesters in the presence of an amount of low molecular weight and low boiling point alcohols having 1–4 carbon atoms per molecule sufficient to provide from about 2 to about 10 moles of OH equivalents per mole of ethylene glycol in the polyesters and an organometallic catalyst at a temperature from about 200° C. to about 300° C.;

(c) the excess alcohol being sufficient to provide for dissolving and crystallizing resulting dialkyl aromatic esters; and (d) filtering and separating of the alcohols, glycols and dialkyl aromatic esters.

2. A chemical process for treating polyesters of o-, m-, and p-bencendicarboxilic acids according to claim 1 wherein the alcoholysis reaction is carried out by the use of methanol.

3. A chemical process for treating polyesters of o-, m-, and p-bencendicarboxilic acids according to claim 1 wherein the organometallic catalysts are selected from the group consisting of cobalt acetate, magnesium acetate, zinc acetate, lithium acetate and alkyl titanates.

4. A chemical process for treating polyesters of o-, m-, and p-bencendicarboxilic acids according to claim 1 wherein the process operating pressure is from about 3.0 to about 10.0 MPa gauge, and the time of reaction is between about 10 to about 100 minutes.

5. A chemical process for treating polyesters of o-, m-, and p-bencendicarboxilic acids according to claim 1 wherein the addition of excess alcohols from about 2 to about 10 times of the stoichiometric amount required by the polyesters present in the alcoholysis reaction.

6. A chemical process for treating polyesters of o-, m-, and p-bencendicarboxilic acids according to claim 1 wherein the dialkyl aromatic esters result along with alcohol and glycols from the alcoholysis reaction of waste polyesters.

7. A chemical process for treating polyesters of o-, m-, and p-bencendicarboxilic acids according to claim 6 wherein the waste polyesters are comprised of poly(ethyleneterephthalate).

8. A chemical process for treating polyesters of o-, m-, and p-bencendicarboxilic acids according to claim 7 wherein the waste poly(ethyleneterephthalate) is comprised of waste bottles.

9. A chemical process for treating polyesters of o-, m-, and p-bencendicarboxilic acids according to claim 8 wherein the waste poly(ethyleneterephthalate) waste bottles are sized to about 4 inches or less.

10. A chemical process for treating polyesters of o-, m-, and p-bencendicarboxilic acids according to claim 1 wherein the process utilizes at least one crystallization cycle, filtration cycle or centrifugation cycle along with recovery and recirculation of alcohol within the process in order to produce and recover dialkyl aromatic esters.

11. A chemical process for treating polyesters of o-, m-, and p-bencendicarboxilic acids according to claim 1 wherein the resulting dialkyl aromatic esters can be utilized to produce bis(2-hydroxiethly)terephthalate (BHET), dimethyl terephthalate (DMT), bis(2-ethylhexyl)terephthalate (DOTP) and terephthalic acid.

* * * * *